(12) United States Patent
Morhain et al.

(10) Patent No.: US 12,172,424 B2
(45) Date of Patent: Dec. 24, 2024

(54) MULTILAYER STRUCTURE FOR DIFFUSION OF VOLATILE SUBSTANCES

(71) Applicant: Zobele Holding SPA, Trento (IT)

(72) Inventors: Cedric Morhain, Barcelona (ES); Livio Sordo, Trento (IT); Stefano Deflorian, Trento (IT)

(73) Assignee: Zobele Holding SPA, Trento (IT)

( * ) Notice: Subject to any disclaimer, the term of this patent is extended or adjusted under 35 U.S.C. 154(b) by 231 days.

(21) Appl. No.: 16/473,903

(22) PCT Filed: Dec. 27, 2016

(86) PCT No.: PCT/EP2016/082693
§ 371 (c)(1),
(2) Date: Jun. 26, 2019

(87) PCT Pub. No.: WO2018/121837
PCT Pub. Date: Jul. 5, 2018

(65) Prior Publication Data
US 2019/0337265 A1    Nov. 7, 2019

(51) Int. Cl.
*B32B 7/06* (2019.01)
*A61L 9/04* (2006.01)
(Continued)

(52) U.S. Cl.
CPC .................. *B32B 7/06* (2013.01); *A61L 9/04* (2013.01); *B32B 5/022* (2013.01); *B32B 5/18* (2013.01);
(Continued)

(58) Field of Classification Search
CPC ..... A61L 9/04; A61L 2209/131; B32B 3/266; B32B 5/022; B32B 5/024; B32B 5/16;
(Continued)

(56) References Cited

U.S. PATENT DOCUMENTS 4,634,614 A * 1/1987 Holzner .................. A61L 9/042
261/DIG. 88
5,518,790 A    5/1996 Huber et al.
(Continued)

FOREIGN PATENT DOCUMENTS

FR    2702961    9/1994
WO    WO 00/09174    2/2000
WO    WO-2016149451 A1 *   9/2016 ............. A61L 9/122

OTHER PUBLICATIONS

English Machine translation for the description of FR 2702961 A1, obtained from ESPACENET (Year: 1994).*
(Continued)

*Primary Examiner* — Aaron Austin
*Assistant Examiner* — Thomas J Kessler
(74) *Attorney, Agent, or Firm* — Sandberg Phoenix & von Gontard, P.C.

(57) ABSTRACT

A multilayer structure (1) for volatile substances diffusers includes a semi-permeable layer (2) that can be in contact with the volatile substances and a barrier layer (3) to prevent the diffusion of the volatile substances before removal of the barrier layer from the multilayer structure. The multilayer structure also comprises a tear layer (4) placed between the barrier layer (3) and the semi-permeable layer (2), which permits the separation of the barrier layer (3) from the semi-permeable layer (2) when the barrier layer (3) is removed from the multilayer structure (1). The tear layer provides a suitable interface strength between the barrier layer and the semi-permeable layer and allows for the secure and easy removal of the barrier layer from the semi-permeable layer.

20 Claims, 1 Drawing Sheet

(51) Int. Cl.
*B32B 5/02* (2006.01)
*B32B 5/18* (2006.01)
*B32B 15/04* (2006.01)
*B32B 15/08* (2006.01)
*B32B 15/14* (2006.01)
*B32B 15/20* (2006.01)
*B32B 27/06* (2006.01)
*B32B 27/08* (2006.01)
*B32B 27/12* (2006.01)
*B32B 27/20* (2006.01)

(52) U.S. Cl.
CPC ............ *B32B 15/046* (2013.01); *B32B 15/08* (2013.01); *B32B 15/14* (2013.01); *B32B 15/20* (2013.01); *B32B 27/065* (2013.01); *B32B 27/08* (2013.01); *B32B 27/12* (2013.01); *B32B 27/20* (2013.01); *A61L 2209/131* (2013.01); *B32B 2250/03* (2013.01); *B32B 2260/021* (2013.01); *B32B 2262/0253* (2013.01); *B32B 2262/062* (2013.01); *B32B 2264/10* (2013.01); *B32B 2266/08* (2013.01); *B32B 2307/7242* (2013.01)

(58) Field of Classification Search
CPC .... B32B 5/18; B32B 7/06; B32B 7/08; B32B 7/12; B32B 15/046; B32B 15/08; B32B 15/14; B32B 15/16; B32B 15/20; B32B 27/065; B32B 27/08; B32B 27/12; B32B 27/14; B32B 27/20; B32B 27/306; B32B 27/36; B32B 2250/03; B32B 2255/06; B32B 2255/10; B32B 2260/021; B32B 2262/0253; B32B 2262/0276; B32B 2262/062; B32B 2264/10; B32B 2266/08; B32B 2307/50; B32B 2307/7242; B32B 2307/732; B32B 2439/00

See application file for complete search history.

(56) References Cited

U.S. PATENT DOCUMENTS 6,358,577 B1* 3/2002 Bowen .................. A61L 9/12
428/35.3
2014/0037922 A1 2/2014 Boyer et al.

OTHER PUBLICATIONS

English Machine translation for the claims of FR 2702961 A1, obtained from ESPACENET (Year: 1994).*
International Search Report dated Nov. 7, 2017 from co-pending International Application No. PCT/EP2016/082693.

* cited by examiner

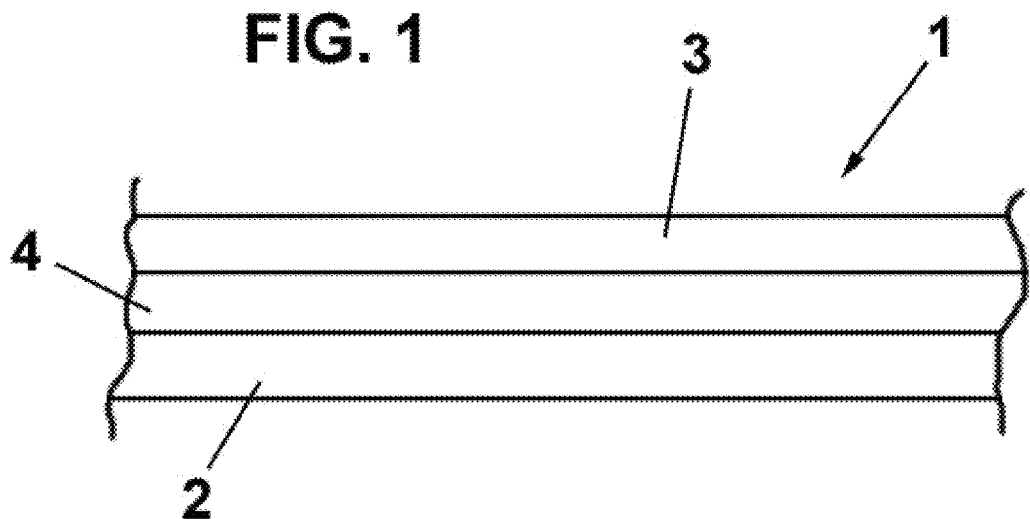
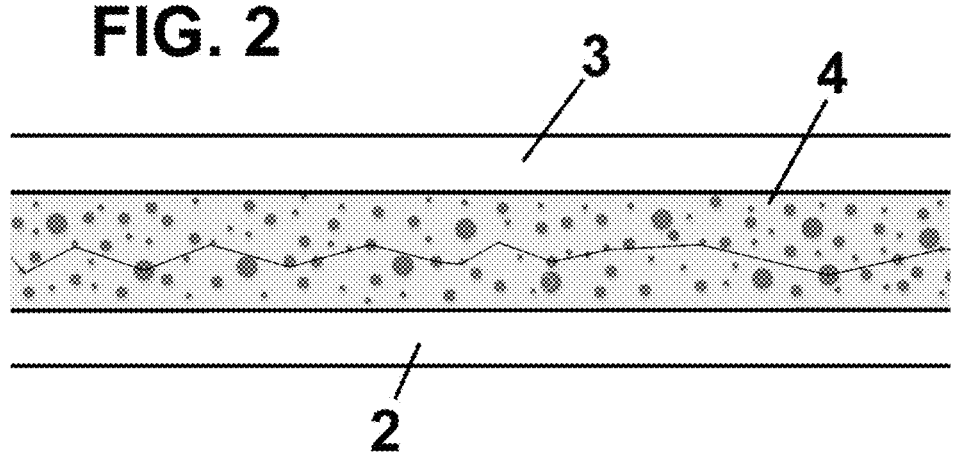

MULTILAYER STRUCTURE FOR DIFFUSION OF VOLATILE SUBSTANCES

CROSS REFERENCE TO RELATED APPLICATION

This application is a U.S. national stage application filed under 35 U.S.C. § 371 of International Patent Application No. PCT/EP2016/082693 filed on Dec. 27, 2016. The entirety of the foregoing application is incorporated by reference herein.

STATEMENT REGARDING FEDERALLY SPONSORED RESEARCH OR DEVELOPMENT

Not applicable.

SEQUENCE LISTING, TABLE OR COMPUTER PROGRAM ON COMPACT DISC

Not applicable.

FIELD OF INVENTION

The present invention is directed to a multilayer structure for diffusion of volatile substances, comprising a barrier layer and a semi-permeable layer.

BACKGROUND OF THE INVENTION

Systems for diffusion of volatile substances with a semi-permeable membrane are well known. These systems comprise a membrane that allows the release of the substance in vapor phase but not in liquid phase.

This membrane can be monolithic or micro-porous. In the case of a monolithic membrane, the transportation of the substance from the inner side to the outer side is done by permeability, and if the membrane is micro-porous, the transportation is mainly done by capillarity.

For both kinds of membranes several solutions have been proposed and have been demonstrated to have a medium to very high performance. Nevertheless, the membrane itself is only one part, even if the most important one, of the system for producing a volatile substance diffuser with a semi-permeable membrane.

Another important part of the system is the part which avoids the evaporation of the volatile substance before its first use by the consumer.

This is generally done by applying a barrier layer on top of the membrane. This barrier layer is removed by the user when he or she wants to use the product for the first time by simply peeling it.

There is a critical point, which is the interface strength between the semi-permeable layer or membrane and the barrier layer. This interface strength should be high enough to avoid accidental activation (separation barrier/membrane) of the diffuser during production or storage. Furthermore, it should be high enough to overcome the pressure generated by the advancing volatile substance that reaches the interface as it passes through the membrane.

The interface strength should be low enough to allow for smooth peeling by the user, without needing a machine for peeling the barrier.

An additional point to be taken into account is that, if the volatile substance is chemically aggressive, it must not weaken the interface, because it must be acceptable after the volatile substance reaches the interface.

One typical defect of unsuitable interface strength between the membrane and the barrier layer is that the volatile substance, after passing through the membrane, is able to create a space for accumulating liquid between the membrane and the barrier layer, which would result in an important leakage when the barrier layer is removed.

Therefore, there is an evident need for a multilayer structure for diffusion of volatile substances that provides for a suitable interface strength between the barrier layer and the semi-permeable layer, and which allows for the secure and easy removal of the barrier layer from the semi-permeable layer.

SUMMARY OF THE INVENTION

With the multilayer structure according to the invention said drawbacks can be solved, presenting other advantages that will be described hereinafter.

The multilayer structure for volatile substances diffusers according to the present invention comprises a semi-permeable layer that can be in contact with the volatile substances and a barrier layer to prevent the diffusion of the volatile substances before the removal of the barrier layer from the multilayer structure, and it is characterized in that it also comprises a tear layer placed between the barrier layer and the semi-permeable layer, which permits the separation of the barrier layer from the semi-permeable layer when the barrier layer is removed from the multilayer structure.

Advantageously, said tear layer is a heterophasic layer. By heterophasic it is understood that the tear layer is composed of areas of high mechanical resistance to tearing and areas of low mechanical resistance to tearing, surrounding the areas of high resistance and behaving as boundaries. The areas of the tear layer include first and second areas, with the first area surrounding the second area. The first area of the tear layer has the first mechanical resistance to tearing and the second area of the tear layer has the second mechanical resistance to tearing. The second mechanical resistance to tearing is higher than or greater than the first mechanical resistance to tearing, whereby, when the first area of the tear layer and the second area of the tear layer are subjected to a same tearing force, the first area of the tear layer tears before the second area of the tear layer tears.

According to two preferred embodiments, said tear layer can comprise particles or fibers, such as, e.g. polyethylene terephtalate or cellulose, in which case, said fibers of the tear layer are joined together by a binder.

Said tear layer can be glued, hot laminated or welded to the barrier layer and/or to the semi-permeable layer.

Advantageously, said tear layer is permeable to the volatile substances, and its thickness is from 20 to 2000 microns, preferably from 20 to 1000 microns, more preferably from 40 to 300 microns, and most preferably from 40 to 150 microns.

The multilayer structure for diffusion of volatile substances according to the invention permits a suitable interface strength between the barrier layer and the semi-permeable layer, which allows for easy and secure removal of the barrier layer from the semi-permeable layer.

BRIEF DESCRIPTION OF THE DRAWINGS

For a better understanding of what has been disclosed, some drawings are attached in which, diagrammatically and only as a non-limitative example a specific embodiment is shown.

FIG. 1 is a diagrammatic cross-section view of the multilayer structure according to the present invention.

FIG. 2 is a diagrammatic cross-section view of the multilayer structure according to the present invention according to a second embodiment, including a mineral filler.

DETAILED DESCRIPTION

FIG. 1 shows the multilayer structure according to the invention in a diagrammatic cross-section view.

This multilayer structure is designed to be placed on a container of products containing volatile substances, such as perfume or insecticide, of a diffuser.

The multilayer structure, generally indicated by numeral reference 1, comprises a semi-permeable layer 2, also known in the art as membrane, which is in contact with the volatile substances, and a barrier layer 3, which prevents the diffusion of the volatile substances before the first use of the diffuser.

According to the invention, the multilayer structure 1 also comprises a tear layer 4, which is placed between the semi-permeable layer 2 and the barrier layer 3. This tear layer 4 permits the separation of the barrier layer 3 from the semi-permeable layer 2 when the diffuser is used for first time.

The tear layer 4 is a weakened heterophasic layer, and according to different embodiments, it can comprise holes or pores, particles without a coupling agent or with lubricant, or fibers, involving weak boundaries inside that layer.

The tear layer 4 can be made of fibers of different materials, preferably cellulose, polyesters, of polyolefins. The fibers have a high mechanical resistance are bounded together either mechanically or by the use of a binder that gives lower mechanical resistance.

Alternatively, as shown in FIG. 2, the tear layer 4 is made of a resin of the same kind than the semi-permeable layer 2, but where some weakening areas have been created by adding mineral fillers. The weight content of mineral filler is preferably higher than 40% and even more preferably higher than 60%. Also, during the process of manufacturing of the tear layer, the material can be stretch in order to create cavities around the filler particles (micropores) in order to have bigger weakened areas that would make easier the tear during activation.

The tear layer 4 can be glued to both the barrier layer 3 and the semi-permeable layer 2. If the glue is permeable to the volatile substances, it can be applied as a continuous layer between both layers 2 and 3. If the glue has low or no permeability to the volatiles substances, if should be applied as a discontinuous layer, such as a grid template, on the semi-permeable layer, in order not to reduce evaporation once the system has been activated.

Alternatively, the tear layer 4 can be welded directly to the semi-permeable layer 2. This can be done in two ways: on one side, if the tear layer 4 is made from plastic with a high compatibility with the semi-permeable layer 2, also made from plastic, it can be welded directly in a calendering process. Otherwise, if the tear layer 4 is micro-porous, it can be joined to the semi-permeable layer 2 by fusion bonding, so that the molten plastic of the semi-permeable layer 2 gets inside the porous structure of the tear layer 4 and when it cools down, it remains mechanically joined.

Furthermore, the tear layer 4 is permeable to the volatile substances, monolithic or micro-porous, and it preferably does not limit the volatile substance transportation.

When the barrier layer 3 is removed, the weakest point of the multilayer structure 1 is the tear layer cohesive strength and the tear layer 4 breaks within its thickness, remaining part of it on the side of the semi-permeable layer 2 and part of it on the side of the barrier layer 3.

The semi-permeable layer 2 can be micro-porous or monolithic and can comprise a backing structure, made from woven or non-woven textile.

The semi-permeable layer 2 can be made from polypropylene, polyethylene, polyurethane, elastomeric polyester, polyether block amide or silicone forming a monolithic tear layer with a thickness from 20 to 2000 microns, preferably 40 to 150 microns.

Furthermore, the semi-permeable layer 2 can be made from micro-porous polyethylene, polypropylene or ultra-high-molecular-weight polyethylene with a thickness from 20 to 1000 microns, preferably 40 to 300 microns.

The barrier layer 3 is preferably made from aluminum, even though it can also be made from plastic, such as ethylene vinyl alcohol or polyvinylidene difluoride, or nanomaterials. The barrier layer 3 can be coated on one or both sides with suitable materials, such as lacquer for protection against oxidation, or polyethylene terephthalate for mechanically reinforcing the barrier layer 3.

Hereinafter three examples of the tear layer are disclosed:

1. The tear layer is a fibrous agglomerate that is made from polymeric fibers (such as polyethylene terephthalate or cellulose) joined together by a binder, and it is glued with a polyurethane membrane, which provides a good permeability for the volatile substances.
2. The tear layer is made from the same material as the semi-permeable layer and is applied by hot lamination on the semi-permeable layer. The tear layer comprises mineral fillers for reducing the mechanical resistance, and it is glued to the barrier layer.
3. The tear layer is made from closed-cells foamed material, which material is the same as the material of the semi-permeable layer. The tear layer is hot laminated on the semi-permeable layer and it is glued on to the barrier layer.

Even though reference is made to a specific embodiment of the invention, it is apparent for a person skilled in the art that the multilayer structure is susceptible of numerous variations and modifications, and all the details cited can be substituted by other technically equivalent ones, without departing from the scope of protection defined by the attached claims.

What is claimed is:

1. A multilayer structure for volatile substances diffusers, the multilayer structure comprising:
    a semi-permeable layer that is exposed to contact with the volatile substances;
    a barrier layer to prevent the diffusion of the volatile substances before removal of the barrier layer from the multilayer structure; and
    a tear layer placed between the barrier layer and the semi-permeable layer permitting the separation of the barrier layer from the semi-permeable layer when the barrier layer is removed from the multilayer structure, the tear layer is a heterophasic layer composed of areas of higher mechanical resistance and areas of lower mechanical resistance surrounding the areas of higher mechanical resistance and behaving as boundaries that remains partially on both the semipermeable layer and the barrier layer after activation, wherein said tear layer comprises fibers that are bound together either mechanically or by use of binder.
2. The multilayer structure for volatile substances diffusers according to claim 1, wherein said tear layer is micro-porous.

3. The multilayer structure for volatile substances diffusers according to claim 1, wherein said tear layer is glued to either or both of the barrier layer and the semi-permeable layer.

4. The multilayer structure for volatile substances diffusers according to claim 1, wherein said tear layer is hot laminated to either or both of the barrier layer and the semi-permeable layer.

5. The multilayer structure for volatile substances diffusers according to claim 1, wherein said tear layer is welded to either or both of the barrier layer and the semi-permeable layer.

6. The multilayer structure for volatile substances diffusers according to claim 1, wherein said tear layer is permeable to the volatile substances.

7. The multilayer structure for volatile substances diffusers according to claim 1, wherein the thickness of said tear layer is from 20 to 1000 microns.

8. The multilayer structure for volatile substances diffusers according to claim 1, wherein the thickness of said tear layer is from 40 to 300 microns.

9. The multilayer structure for volatile substances diffusers according to claim 1, wherein the thickness of said tear layer is from 40 to 150 microns.

10. A multilayer structure for volatile substances diffusers, the multilayer structure comprising:
   a semi-permeable layer that is exposed to contact with the volatile substances;
   a barrier layer to prevent the diffusion of the volatile substances before removal of the barrier layer from the multilayer structure;
   a tear layer placed between the barrier layer and the semi-permeable layer permitting the separation of the barrier layer from the semi-permeable layer when the barrier layer is removed from the multilayer structure, the tear layer is a heterophasic layer comprised of areas of higher mechanical resistance to tearing and areas of lower mechanical resistance to tearing surrounding the areas of higher mechanical resistance to tearing and behaving as boundaries that remain partially on both the semi-permeable layer and the barrier layer after activation;
   the tear layer is comprised of first and second areas, the first area of the tear layer surrounds the second area of the tear layer, the first area of the tear layer having a first mechanical resistance to tearing, the second area of the tear layer having a second mechanical resistance to tearing, the second mechanical resistance to tearing being higher than the first mechanical resistance to tearing, whereby, when the first area of the tear layer and the second area of the tear layer are subjected to a same tearing force, the first area of the tear layer tears before the second area of the tear layer tears.

11. The multilayer structure for volatile substances diffusers according to claim 10, wherein the tear layer is glued to at least one of the barrier layer and the semi-permeable layer.

12. The multilayer structure for volatile substances diffusers according to claim 10, wherein the tear layer is hot laminated to at least one of the barrier layer and the semipermeable layer.

13. The multilayer structure for volatile substances diffusers according to claim 10, wherein the tear layer is welded to at least one of the barrier layer and the semi-permeable layer.

14. The multilayer structure for volatile substances diffusers according to claim 10, wherein the tear layer is permeable to volatile substances.

15. The multilayer structure for volatile substances diffusers according to claim 10, wherein the tear layer comprises fibers.

16. The multilayer structure for volatile substances according to claim 15, wherein the fibers of the tear layer are joined together by a binder.

17. A multilayer structure for volatile substances diffusers, the multilayer structure consisting of:
   a semi-permeable layer that is exposed to contact with the volatile substances;
   a barrier layer to prevent the diffusion of the volatile substances before removal of the barrier layer from the multilayer structure;
   a tear layer placed between the barrier layer and the semi-permeable layer permitting the separation of the barrier layer from the semi-permeable layer when the barrier layer is removed from the multilayer structure, the tear layer is a heterophasic layer comprised of areas of higher mechanical resistance to tearing and areas of lower mechanical resistance to tearing surrounding the areas of higher mechanical resistance to tearing and behaving as boundaries that remain partially on both the semi-permeable layer and the barrier layer after activation;
   the tear layer is comprised of first and second areas, the first area of the tear layer surrounds the second area of the tear layer, the first area of the tear layer having a first mechanical resistance to tearing, the second area of the tear layer having a second mechanical resistance to tearing, the second mechanical resistance to tearing being higher than the first mechanical resistance to tearing, whereby, when the first area of the tear layer and the second area of the tear layer are subjected to a same tearing force, the first area of the tear layer tears before the second area of the tear layer tears.

18. The multilayer structure for volatile substances diffusers according to claim 17, wherein the tear layer is permeable to volatile substances.

19. The multilayer structure for volatile substances diffusers according to claim 17, wherein the tear layer comprises fibers.

20. The multilayer structure for volatile substances according to claim 19, wherein the fibers of the tear layer are joined together by a binder.

* * * * *